HYDRID TEA ROSE PLANT
Filed March 5, 1973
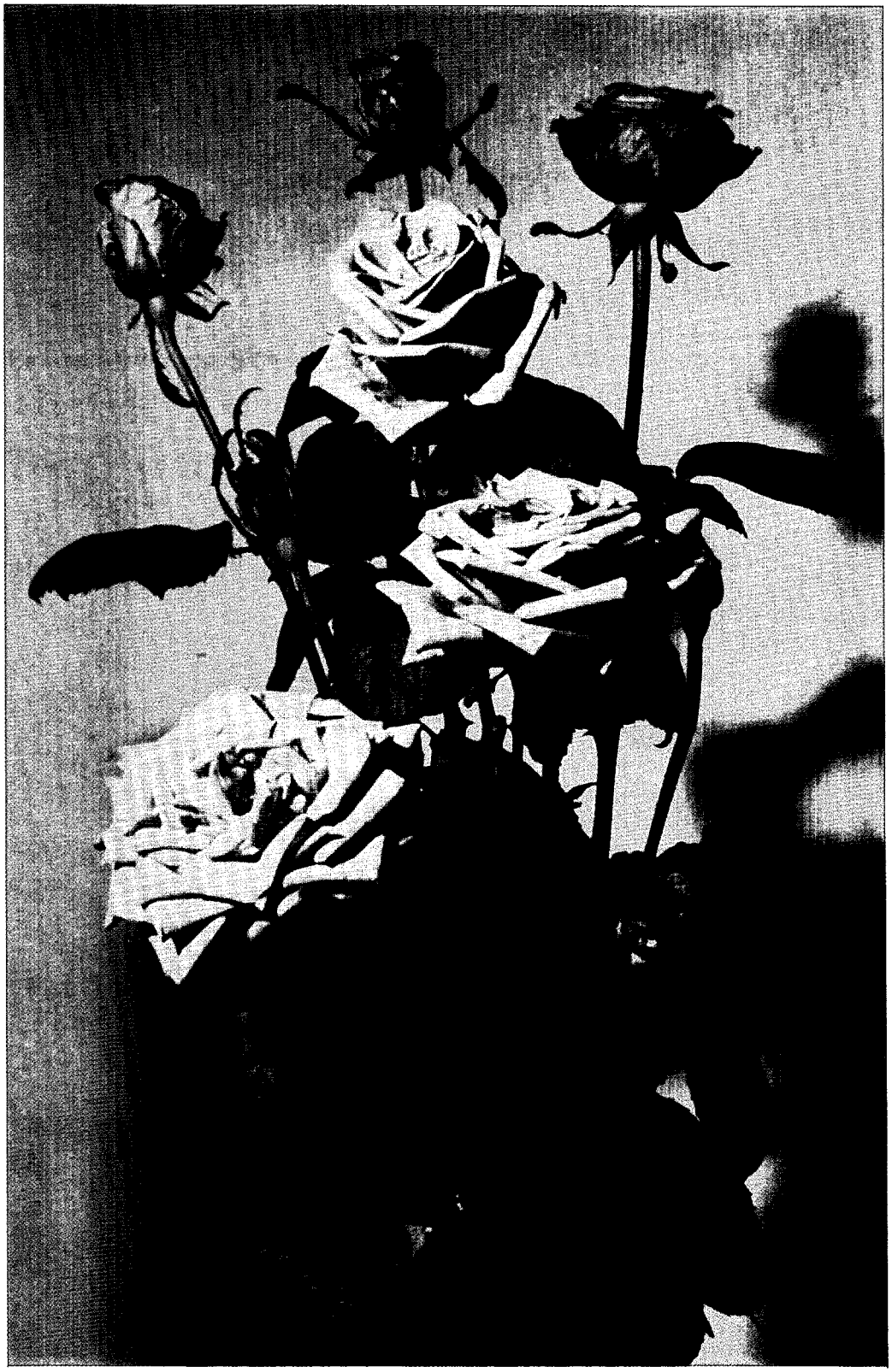

United States Patent Office

Plant Pat. 3,653
Patented Nov. 19, 1974

3,653

HYBRID TEA ROSE PLANT

Armando Valepiano and Sergio Valepiano, both of Via Forte San Paolo 27, Ventimiglia, Italy 00139

Filed Mar. 5, 1973, Ser. No. 338,220
Claims priority, application Italy, Mar. 3, 1972, 48,755/72
Int. Cl. A01h *5/00*
U.S. Cl. Plt.—20 1 Claim

ABSTRACT OF THE DISCLOSURE

A hybrid tea rose plant is disclosed, having medium-sized flowers, the color of which is from Turkey Red to Orient Red.

BACKGROUND OF THE INVENTION

The present invention relates to a new variety of hybrid tea rose, obtained by the applicants in the course of their horticultural activities and more particularly as a result of their search for new varieties of roses for large-scale cultivation for cut-flower production. In the course of this research, the applicants noted that a plant of the variety of rose commercially known as Baccara had a tendency to produce, on a few branches, flowers different from those typical of the variety. The stems also tended to depart from the norm of Baccara rose characteristics.

In particular, the stems were more sturdy, articulated in more slender and aesthetically pleasing internodes, while the flower corolla was more ample, longer, and of a different red than that generally found on a Baccara rose. The new variety is distinguishable from the latter from the point of view of the properties mentioned, which constitute an improvement over the mutant type of plant.

The applicants have therefore carried out lengthy research and made numerous attempts to isolate the new mutation which had been observed on the plant. Had the applicants not intervened at this point, the mutation would have remained unknown, and disappeared with the mutant plant. A long series of propagations of buds selected from the mutant branches of the Baccara variety of the plant permitted a precise selection of the improved properties and their fixation in the new variety which is the subject of the present invention.

The accompanying drawing shows typical specimens of the vegetative growth and flowers of our new variety in different stages of development, as depicted in color as nearly true as it is reasonably possible to make the same in a color illustration of this character.

DESCRIPTION OF THE INVENTION

Thus a plant has been obtained that is distinguishable from the original Baccara plant as well as from all the other varieties of its class. The new properties introduced by the selection of the mutant parts are transmitted in a constant and faithful manner to all the specimens that have been grown so far. As a result, the new variety may be easily cultivated on an industrial scale for the production of cut flowers as well as for bushes to decorate rooms and gardens.

The variety which is the subject of the present invention, obtained as indicated above, may be reproduced easily and propagated in any number of specimens, all of them having the properties of the original plant, by means of one of the development methods of plant propagation used in flower cultivation, and preferably by taking from the original plant, or from another plant derived from it, an "eye" or auxiliary bud which is then grafted onto a recipient plant, of a species adapted to the soil and climactic conditions under which cultivation is going to be carried out.

It is thus possible to obtain numerous identical specimens of the variety which is the subject of the present invention, with all the distinctive properties of the original plant. These properties, which distinguish the object of the present invention from other varieties of its class and permit its identification, are listed, by way of example and without any limitations, in the following description based on a set of plants cultivated by industrial methods, grafted a year previously onto *Rosa indica major* stock, and grown in unheated glasshouses on a sunny hillside in Ventimiglia (Italy), the description being that of the plants in the month of January.

Reference should always be made to these climactic and seasonal conditions in any comparison of this variety made as a function of the present description. Any possible differences which, as a result of different conditions of climate, soil or method of cultivation, may be encountered between certain features of the plant and the corresponding ones of the description must be considered normal, and modify in no manner the essence of the present invention, at least, so long as it is possible to identify the plant by means of the collection of features given in the description hereinbelow, by repeating the cultivation under the same conditions as those of the plants described.

In the description, the colors have been named according to the tables of the "Horticultural Color Chart" by Robert F. Wilson (indicated in the text by the initials HCC) except in those cases in which the colors were absent from the tables or where its indication was sufficiently clear in common parlance.

Classification: Hybrid tea.

Stock: Sport of the Baccara variety

PLANT

Growth: Bushy, with slender, vertical growth of average compactness.

Average Height: About 150–200 cm. from the ground for fully developed plants cultivated as described above.

Roots: Of variable shape and size according to the type of graft recipient used for the propagation. In the plants described, the roots were averagely numerous, starting radially from the collar and going straight down, averagely ramified with averagely developed root hairs. Average length 30–40 cm. Average diameter at the collar 4 mm.

Stem: Of variable shape and size according to the type of graft recipient used for the propagation. In the plants described, the main stem was constituted by the *Rosa indica major* recipient, of an average length of 20–25 cm. and an average diameter at the collar of 10–12 cm.

Main Branches: Fairly numerous, average number 4–6, starting from the grafting point and from the stem at close intervals.

*Shape.*—Approximately cylindrical, diameter gradually decreasing from the tip to the bottom, slightly divergent from the axis of the plant and then more vertical and parallel, straight or only slightly sinuous, articulated in intermodes 40–70 mm. long on average. Nodes slightly or averagely differentiated, standing out only slightly from the branches. Dimensions average, variable according to the method of pruning. Average length 40–60 cm., average diameter at the base 8–12 mm.

*Bark.*—Smooth, hairless, opaque. Color close to Lavender green (HCC p. 196 shade 000761) frequently well covered with Royal purple (HCC p. 174 shade 834/3).

*Thorns.*—Fairly numerous to numerous, well distributed on the branches, of variable size, not easily removed, intermixed with very small thorns. Shape—Large triangular thorns, with slender tip, differentiated, set at a right angle to the stem or slightly tilted downwards. Lower side concave. Oval, spear-shaped base, elongate towards the base. Small thorns—same shape as the large. Size—large thorns, average length 6–8 mm., breadth 8–10 mm., thickness 3–4 mm. Small Thorns, average length 1–4 mm., average breadth 1–3 mm., thickness 0.5–1 mm. Color—close to Garnet brown (HCC p. 192, shades 00918/2–3). Consistency — semi-woody, hard, resistant. Shape—triangular with curved sides and lower side concave. Sharp and differentiated tip slightly tilted downwards and straight. Oval, elongated base. Thorns averagely detachable from the bark. Size—average length 7–10 mm., width 12–18 mm., thickness 3–4 mm. Color—close on Erythrite red (HCC p. 190 shades 0027/1–2).

Leaves: Large, numerous, sited individually on each node, sparse on the branches. They cover the plant over the whole of its height in an elegant manner.

*Shape.*—Averagely long and wide, composed of 3–5–7 folioles inserted in opposing pairs plus a terminal foliole on a sturdy rachis, straight or slightly sinuous. The leaves having 7 folioles are more frequent lower on the plant, those having 5 towards the middle and those having 3 at the top.

Flower Stems: Averagely numerous, on average from 3 to 5 on each main branch, inserted at varying heights on the main branches, and sometimes formed at their tips.

*Shape.*—Practically cylindrical, sturdy, fairly thick to thick, the diameter diminishing little from the base to the top, straight or slightly sinuous, sometimes slightly angulate in correspondence with the nodes, articulated in numerous internodes of widely different lengths, from 20 to 100 mm. or more. Nodes fairly differentiated, standing out little from the stems.

*Size.*—On average 800–1300 mm. long, diameter 6–10 mm. at the base.

*Bark.*—Smooth, hairless, satiny, pruinose in places.

*Color.*—Close to Parsley green (HCC p. 193 shades 00962/1), intermingled in places with Pansy Purple (HCC p. 177, shades 928/2–3).

*Thorns.*—Fairly numerous, large, of uniform size, scattered on stems, on average from 5 to 8 per internode, more closely spaced towards the base of the stems, sometimes intermingled with other, smaller thorns, not very or fairly numerous.

*Folioles.*—Generally flat or slightly upturned in relation to the plant of the leaf, perpendicular to the rachis, or as far as the first pair starting from the base is concerned, obliquely inclined toward the base of the leaves.

*Size.*—Variable according to the stage of development, varying little according to the position on the stem. Average length from attachment to tip of terminal foliole 120–150 mm., width between opposite foliole extremities 80–130 mm.

*Bearing.*—Diverging from the stem to become almost horizontal, even sometimes slightly upturned with terminal foliole curved downwards.

*Foliole.*—Big limb, flat or slightly curved downwards at the edges, oval, average rounded, averagely differentiated little points situated at the summits of the folioles. Outer edge serrated with teeth of average size or large size, clear-cut, pointed. Edges serrated towards the base with very short teeth not much in evidence. Petioles of the foliole short and cylindrical. Average size varying according to position on the rachis, increasing from the base towards the terminal foliole on average as follows: Leaves with 7 folioles, first pair starting from the base, length 30–40 mm., breadth 20–25 mm. Second pair length 40–50 mm., breadth 25–30 mm. Third pair, length 45–55 mm., breadth 30–35 mm. Terminal foliole length 50–55 mm., breadth 40–50 mm. Leaves with 5 folioles: First pair starting from the base, length 40–50 mm., breadth 30–35 mm. Second pair, length 50–55 mm., breadth 35–40 mm. Terminal foliole, length 60–70 mm., breadth 35–50 mm. Leaves with 3 folioles: lateral leaves, length 35–55 mm., breadth 35–40 mm. Terminal leaves length 70–80 mm., breadth 50–60 mm.

*Color.*—Upper face—between Leek green (HCC p. 197, shade 000858) and Ivy green (HCC p. 200, shade 0001060/3). Lower face—close to Lavender green (HCC p. 196, shade 000761) or even mixed with purple madder (HCC p. 181, shades 1028/1.2.3).

*Surface.*—Upper face—smooth, hairless, opaque or averagely shiny, sometimes slightly bubbly between nervations. Feathered nervations fairly concave in the limb. Lower face—smooth, hairless, opaque with feathered nervations, differentiated protruding on the limb.

*Consistency.*—Tough, thick, resistant.

Rachis: Sturdy, with a longitudinal furrow fairly marked, with hairy edges, sometimes tinted with purple madder (HCC p. 181, shades 1028/1.2.3). Rachis divided at regular intervals starting from the fork of the folioles. Longer internodes in the middle section.

Stipulae: Straight or averagely straight, clustered at the base of the rachis up to the first third of the first internode of the latter. Fine triangular ears having serrated and hairy edges, forming an angle of 30–40° with the rachis.

FLOWER

Bearing: Main flower single at the apex of the stem, sometimes accompanied by several secondary buds borne by thin secondary stems inserted on the highest nodes of the stems, or at the base of the flower-bearing peduncle. Lateral secondary stems sometimes lacking in buds. Sturdy flower-bearing peduncle, straight or slightly sinuous, elongate, cylindrical, having very short, tender, glandular hairs.

Closed Flower Bud: Oval shaped, averagely elongate, with fairly sharp tips, sepal points averagely developed and separate. Very fine filiforme appendices stand out from the bud profile.

*Size.*—Average length 30–35 mm., diameter 18–22 mm., not including the terminal apendices of the sepals which are sometimes absent.

*Calyx.*—Shape—elongated, urn-shaped receptacle, continuing in the flower-bearing peduncle. Opening of the sepals is precocious compared with the petals.

*Sepals.*—Five in number, inserted at the edge of the receptacle, triangular, large, slightly spear-shaped with slender points which even lengthen into leafy appendices over about 40–60 mm., fairly expanded, serrated borders. Other leafy appendices with an average length of 25–30 mm., and breadth reaching 4–5 mm., diverging from the sides of the sepals and giving these latter a laciniated or slashed appearance. Downy edegs to the sepals. Average size: length (without the appendices) 30–35 mm., breadth at the base 8–12 mm.

*Surface.*—Uper face—opaque, slightly downy (tomentose) in the sepals, shiny at the leafy appendices. Lower face—opaque or averagely satin-finished, a little globulous in the sepal; opaque, smooth, hairless, on the leafy appendices.

*Color.*—Upper face—sepals Lavender green (HCC p. 196, shades 000761/2.3), Ivy green (HCC p. 200, shades 0001060/2.3) in the leafy appendices; lower face—Spinach green (HCC p. 187, shades 0960/1.2). Receptacle—color Lettuce green (HCC p. 176, shades 861–61/1).

*Consistency.*—Average thickness, herbaceous, resistant.

Half Open Flower Bud: Elongate urn-shaped, slightly bell-shaped at the top, with a few external petals barely open at first forming a conical urn opening out towards the top, with the edge of the petals curling towards the outside. Sepals open in a star shape, not much drooping towards the receptacle. Outer petals turbinated.

*Size.*—Average length 40–50 mm., diameter 20–30 mm.

*Color.*—Outside of the petals close to Chrysanthemum crimson (HCC p. 169, shades 24–24/1). Inner face of the petals between Turkey red (HCC p. 94, shades 721–21/1) and Orient red (HCC p. 165, shades 819–19/1.2) with flecks of Vermilion (HCC p. 18, shades 18–18/1).

Open Corolla: Shaped like an open, hemispherical cup with the flat part uppermost, well-lined; rounded contour, regular, slightly star-shaped, with imbricated petals, well developed. The outer petals are not much separated from the rest of the corolla, outward furling, forming variously marked points around the flower. Central petals free, well-developed, vertical or slightly inclined to the outside. Irregular central petaloids covering the stamens and pistils. Center of the flower: full, flat, or slightly convex.

*Size.*—Average diameter in wholly open condition 90–110 mm., length of flower from receptacle to apex of petals 40–50 mm.

*General color.*—Between Turkey red (HCC p. 94, shades 721–21/1.2) and Orient red (HCC p. 165, shades 819/1.2.3).

*Petals.*—Numerous, on average 60–70 as well as 8–10 petaloid stamens in the center of the flower, disposed regularly on the receptacle.

*Shape.*—Outer petals—rounded limbs, side edges converging in the claw at angles of between 80 and 90°. Center of the petals concave. Lateral edges curled towards the outside. Smooth edges, slightly corrugated and festooned. Some external petals forming a cluster with the sepals, and more or less open curls. Small, differentiated claw. Inner petals—substantially the same shape as the outer petals, but slightly more elongate, concave at the center. Outside edges smooth, fairly corrugated, slightly curved towards the outside. The petals in the center have an irregular limb with deeply furled festoons.

*Size.*—Outer petals: length 50–60 mm., breadth 50–60 mm. Inner petals: length 30–40 mm., breadth 30–40 mm.

*Color.*—Front side of petals, between Turkey red (HCC p. 94, shades 721–21/1) and Orient red (HCC p. 166, shades 819–19/1.2) with light Vermilion tones (HCC p. 18, shades 18–18/1). Lower face outer part close to Chrysanthemum crimson (HCC p. 169, shades 824–24/1).

*Surface.*—Upper face velvety, Lower face satiny.

*Consistency.*—Thick, fairly fleshy, resistant.

Organs of Reproduction: Stamens—numerous, on average 90–120, inserted on the edge of the receptacle. Filaments erect, slender, slightly curved towards the styles, length up to 7–10 mm., whitish with purple tinges. Anthers large, spear-shaper, bilocular; length 4–5 mm. and breadth 1–2 mm. Styles are numerous, on average 100–110, with a thick down, wooly at the base, extremely fine, straight or slightly curved length up to 18–20 mm. Greenish white at the base, tinged with purple at the distal extremity. Ovarium contained within the receptacle.

Scent: Noticeable, slight tones of tea.

Resistance of Flowers to Inclemency of Weather: Very good.

Resistance of Flowers to Transport: Very good.

Resistance of Flowers Once Cut: Remarkable.

Resistance of Plant to Disease: Very good.

Simplicity of Cultivation: Very good.

Capacity to Reflower: Abundant and continuous.

Ease of Grafting: Very good.

What is claimed is:

1. A hybrid tea rose plant, having medium sized flowers, colored between Turkey red, Orient red, characterized in that the first plant of this variety was obtained by isolating a sport of the variety of rose commercially known by the name of Baccara, and said plant having the following unique combination of characteristics:

a. *from the physical standpoint:* a plant that is vigorous, bushy, and slender and is of average density, growing to an average height of 150–200 cm. from the ground, with numerous branches and flowers; stems are not widely spaced and are well covered with large leaves of a dark green that matches the flowers harmoniously; the flowers are from average to large in size, of harmonious shape, of a color between Turkey red and Orient red with tinges of red Vermilion, and are suitable for commerce and export;

b. *from a physiological standpoint:* a plant that is resistant to disease, that is simple to grow for industrial production and which has considerable vegetative affinity for the main graft recipients; the flowers of which are resistant to the inclemencies of weather and to discoloration from sunlight, withstand transport and packing well, and which last well after being cut; and the flowers and other parts of the plant being suitable for reproduction by vegetative means.

References Cited

UNITED STATES PATENTS

| | | | |
|---|---|---|---|
| P.P. 2,545 | 7/1965 | Samtmann | 20 |
| P.P. 3,321 | 5/1973 | Molina | 20 |

ROBERT E. BAGWILL, Primary Examiner